United States Patent
Lokot

(10) Patent No.: US 10,034,838 B2
(45) Date of Patent: Jul. 31, 2018

(54) TARGETED DELIVERY OF HYDROPHILIC DRUGS

(71) Applicant: Double Bond Pharmaceuticals AB, Uppsala (SE)

(72) Inventor: Igor Lokot, Uppsala (SE)

(73) Assignee: DOUBLE BOND PHARMACEUTICALS AB, Uppsala (SE)

( * ) Notice: Subject to any disclaimer, the term of this patent is extended or adjusted under 35 U.S.C. 154(b) by 8 days.

(21) Appl. No.: 15/509,875

(22) PCT Filed: Sep. 9, 2015

(86) PCT No.: PCT/SE2015/000055
§ 371 (c)(1),
(2) Date: Mar. 9, 2017

(87) PCT Pub. No.: WO2016/039678
PCT Pub. Date: Mar. 17, 2016

(65) Prior Publication Data
US 2017/0239192 A1    Aug. 24, 2017

(30) Foreign Application Priority Data
Sep. 10, 2014    (SE) ...................................... 1400427

(51) Int. Cl.
| | | |
|---|---|---|
| *A61K 9/51* | (2006.01) | |
| *A61K 31/55* | (2006.01) | |
| *A61K 31/136* | (2006.01) | |
| *A61K 31/4745* | (2006.01) | |
| *A61K 9/00* | (2006.01) | |
| *A61K 31/704* | (2006.01) | |

(52) U.S. Cl.
CPC .......... *A61K 9/5123* (2013.01); *A61K 9/0019* (2013.01); *A61K 31/136* (2013.01); *A61K 31/4745* (2013.01); *A61K 31/55* (2013.01); *A61K 31/704* (2013.01)

(58) Field of Classification Search
None
See application file for complete search history.

(56) References Cited

U.S. PATENT DOCUMENTS

2012/0269722 A1    10/2012   Lewis et al.

FOREIGN PATENT DOCUMENTS

| | | |
|---|---|---|
| GB | 2415904 A | 1/2006 |
| KR | 20140095438 A | 8/2014 |
| WO | 99/47543 A2 | 9/1999 |
| WO | 03/099346 A2 | 12/2003 |
| WO | 2009/078756 A1 | 6/2009 |
| WO | 2009/100222 A1 | 8/2009 |

OTHER PUBLICATIONS

Gu "A Novel Approach to Formulations of Anticancer Drugs in Nanoparticles" 2008.*
Enache, M. et al., Coupled spectral and electrochemical evaluation of the anticancer drug mitoxantrone-sodium dodecyl sulfate interaction, International Journal of Pharmaceutics, vol. 390, No. 2, pp. 100-106 (2010).
Gu, Xinyi, A novel approach to formulation of anticancer drugs in nanoparticles, Dissertation, The University of Michigan, pp. 1-170 (2008).

* cited by examiner

*Primary Examiner* — Robert A Wax
*Assistant Examiner* — Danah Al-Awadi
(74) *Attorney, Agent, or Firm* — Porter Wright Morris & Arthur LLP

(57) ABSTRACT

A pharmaceutical composition in form of an aqueous colloid or an aqueous suspension of particles up to a size of 100 μm comprises or consists of amphiphilic sulfonate or sulfate of a hydrophilic cancer drug having a solubility in water or aqueous body fluid of less than 0.1% by weight. Also disclosed are the particles in powderous form, methods for their production and for the production of the colloid and the courser suspension, a method of treating liver cancer, in particular solid liver cancer tumours, by administration of the pharmaceutical composition, and a method of designing a composition according to the invention.

29 Claims, 5 Drawing Sheets

TARGETED DELIVERY OF HYDROPHILIC DRUGS

FIELD OF THE INVENTION

The present invention relates to the administration of hydrophilic drugs to the liver of a human or animal, and to a solid liver tumour. More specifically the present invention relates to the administration of hydrophilic drugs, in particular anti-cancer drugs.

BACKGROUND OF THE INVENTION

The therapeutic window represents the range of drug dosages by which a disease can be treated efficiently and safely. It ranges from the dosage at which a noticeable therapeutic effect is seen to that at which the therapeutic benefit is neutralized by adverse effects.

The majority of anticancer drugs have a narrow therapeutic window. In addition it is often a tiny fraction of an administered dose that reaches the site to be treated. Upon systemic administration by oral ingestion or intravascular injection, the medication is distributed throughout the body via the circulation resulting in the entire body being affected. Ideally, the medication should be directed exclusively to a desired body site such as an organ or tissue in need of treatment. Such targeted administration would avoid harming the rest of the body. This kind of administration seeks to direct the medication to tissues of interest while avoiding substantial amounts thereof reaching tissues that do not require treatment.

An example of drugs which need to be directed to a specific body site is the anti-cancer drug doxorubicin. It is generally accepted that the therapeutic potential of doxorubicin could be significantly improved by targeted drug delivery since its dangerous side effects thereby could be avoided or at least substantially reduced. The most dangerous side effect of doxorubicin is damage to the heart. When the cumulative dose of doxorubicin reaches 550 mg/m$^2$, the risk of developing cardiac side effects increases dramatically. Doxorubicin cardiotoxicity is characterized by a dose-dependent decline in mitochondrial oxidative phosphorylation. Reactive oxygen species generated by the interaction of doxorubicin with iron can damage myocytes causing myofibrillar loss and cytoplasmic vacuolization. Excessive damage of this kind may result in the death of the patient. It is therefore desirable to keep the cardiac concentration of doxorubicin as low as possible.

Liver cancer is one of a number of malignancies in which administration of doxorubicin is indicated. More specifically, liver cancer can be treated by targeted (or local) administration in a procedure known as transarterial chemo-embolization. In this procedure doxorubicin is administered through a catheter directly to artery(ies) feeding the diseased portion of the liver while arteries supplying portions of the liver not affected by the disease are blocked by, for instance, gelatin sponge.

Isolated liver perfusion is one approach for targeted delivery of drugs to the liver. It comprises a surgical procedure during which the circulation of blood to the liver is separated from general circulation and separately perfused with blood. After separation the drug is injected into the blood by which the liver is being perfused, allowing a higher concentration of chemoterapeutical agent(s) to be used than with systemic administration. This invasive procedure is however technically complicated and not safe.

Many pharmacologically active agents such as the aforementioned anti-cancer drugs are week bases in that they comprise one or more amino groups. For this reason they form salts with strong and weak acids, and are usually administered in salt form. The solubility of their common pharmaceutically acceptable salts, in particular their hydrochlorides, hydrobromides, phosphates, sulfates, lactates, tartrates, etc. in aqueous body fluid is usually higher than the solubility of the free base. Therefore aqueous solutions of such salts are used for intravenous infusion rather than an aqueous solution of the respective base.

For administration to the liver of a person or animal anti-cancer drugs of this kind are provided in a cationic amphiphilic form (in the form of a salt with a pharmaceutically acceptable acid). This manner of administration is applied but not limited to anti-cancer drugs such as, for instance, anthracyclines (doxorubicin, epirubicin, daunorubicin, idarubicin, mitoxantrone), *vinca* alkaloids (vinblastine, vincristine, vinorelbine), amsacrine, topotecan and irinotecan. If a pharmacologically active agent comprises more than one amino group two or more of them may be protonated and form salts with an acid.

Cationic amphiphilic drugs (CAD) of the aforementioned kind react with amphiphilic anionic surfactants, such as alkyl sulfates or alkane sulfonates, to form water insoluble complexes.

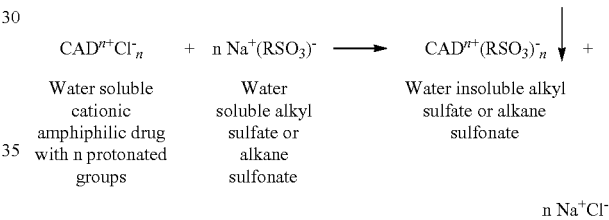

While still meeting the definition of a salt of an organic base with an organic or inorganic acid, the water insoluble complexes are to some extent additionally linked by non-covalent forces.

Objects of the Invention

A primary object of the invention is to provide a pharmaceutical composition for targeted administration to the liver of an anti-cancer drug comprising one or more amino functions, which is lacking one or more of the drawbacks of known compositions of the drug or at least exhibits them to a lesser extent.

Another object of the invention is to provide a pharmaceutical composition for targeted administration to a solid liver tumour of an anti-cancer drug comprising one or more amino functions, which is lacking one or more of the drawbacks of known compositions of the drug known in the art or at least exhibits them to a lesser extent.

A further object of the invention is to provide a method of designing pharmaceutical compositions of this kind that will provide, after intravenous administration, a desired target concentration of the drug in the liver or the solid liver tumour.

Additional objects of the invention will become evident from the study of the following short description of the invention, of preferred embodiments thereof, and of the appended claims.

SUMMARY OF THE INVENTION

The present invention is based on the insight that aqueous suspensions of particles of amphiphilic compounds, in particular of straight chain alkyl sulfonates and straight chain alkane sulfates of hydrophilic anti-cancer drugs comprising amino function(s), are valuable forms by which these drugs can be administered in a manner concentrating their therapeutic effect to the liver or the solid liver tumour, i.e., targeting the liver or solid tumour. Thus, by targeting is understood preferential delivery to the liver so as to achieve a higher drug concentration (w/w) in liver tissue, including liver cancer tissue, than in other tissues. An important feature of straight chain alkyl sulfonates and of straight chain alkane sulfates of hydrophilic anti-cancer drugs is their low solubility in water and aqueous body fluid of less than 0.1 mg/mL at 25° C.

A possible explanation of the biology behind the invention, which is however in no way binding, is that upon administration of a particulate aqueous suspension of an anti-cancer drug of this kind to the systemic circulation or the liver or a solid liver tumour the drug particles will reach, within a given period of time, an equilibrium distribution in the body. Their solubility in aqueous media is very low but not nil. The will therefore slowly dissolve in body fluid until an equilibrium determined by their solubility is reached. Since the dissolved material is irreversibly transformed chemically to degradation products more material is dissolved over time to maintain the equilibrium. As long as the equilibrium is fed by dissolving material a steady state concentration of the drug is maintained locally.

The present invention is furthermore based on the insight that aqueous colloids of amphiphilic straight chain alkyl sulfonates of hydrophilic anti-cancer drugs comprising amino function(s) and of amphiphilic straight chain alkane sulfates of hydrophilic anti-cancer drugs comprising amino function(s) are particularly valuable forms by which these drugs can be administered in a manner concentrating their therapeutic effect to the desired organ, in particular the liver, or to the desired solid tumour, i.e., targeting the organ or solid tumour. Aqueous colloids are constituted by particles or comprise particles of a size of up to about 10000 nm.

An important property of aqueous colloids of the invention is their low sedimentation rate. In general the sedimentation rate of a given sort of particle increases with particle size. It may however be prevented from increasing and even be decreased by increasing the viscosity of the aqueous phase and/or by changing a surface property of the particles, such as, for instance, surface roughness.

The present invention provides solid particles of a salt of a hydrophilic cancer drug comprising one or more amino groups and a water soluble alkyl sulfate or alkane sulfonate or a mixture of two or more of such sulfates or sulfonates. An important feature of the salt is its low solubility in water. In other words, the salts of the invention are substantially insoluble. By "substantially soluble" is understood a solubility in water or aqueous body fluid of less than 0.1% by weight, in particular of less than 0.05 or 0.02 by weight.

The present invention provides a method of producing said solid particles of a water insoluble salt of a hydrophilic cancer drug with a water soluble alkyl sulfate or alkane sulfonate or with a mixture of two or more of such sulfates or sulfonates.

The present invention furthermore provides a pharmaceutical composition comprising one or more amphiphilic sulfonates and/or sulfates of the invention and a liquid carrier. The composition can be administered by any suitable route, such as by intraarterial, intraperitoneal, intramuscular, transdermal or intravenous administration. Administration of a bolus comprising an aqueous colloid of the amphiphilic sulfonates and sulfates of the invention is preferred.

The present invention also provides a method of producing a pharmaceutical composition comprising a water insoluble salt of a hydrophilic cancer drug and a water soluble alkyl sulfate or alkane sulfonate or of a mixture of two or more of such sulfates or sulfonates in form of solid particles.

The composition of the invention may further comprise a buffer and pharmaceutically acceptable excipients such as osmolality controlling agent and viscosity controlling agent. Due to the method of production used the composition additionally contains a salt or corresponding ions consisting of the cation of the water soluble alkyl sulfate or alkane sulfonate and of the anion of the anti-cancer drug. The use of alkali alkyl sulfates and of alkali alkane sulfonates, in particular of sodium and potassium alkyl sulfates and alkane sulfonates, is preferred.

The amphiphilic particulate sulfonates and sulfates of the invention consist of a pharmacological agent D possessing anti-cancer activity comprising from 1 to 4 amino groups of which one or more is protonated, and of one or more sulfate or sulfonate anion. They are represented by formulae (1) and (2):

$$D^{n+}(R^1SO_3)^-_n \quad (1)$$

$$D^{n+}(R^2OSO_3)^-_n \quad (2)$$

wherein $R^1$ is straight chain $C_6$-$C_{30}$ alkyl; $R^2$ is straight chain $C_6$-$C_{30}$ alkyl; n is an integer from 1 to 4.

It is preferred for $R^1$ and $R^2$ to be straight chain $C_{10}$-$C_{20}$ alkyl, more preferred to be straight chain $C_{12}$-$C_{18}$ alkyl, even more preferred to be about straight chain $C_{16}$ alkyl. In consequence, $R^1$ can be any of straight chain $C_{12}$, $C_{13}$, $C_{14}$, $C_{15}$, $C_{16}$, $C_{17}$, $C_{18}$ alkyl; $R^2$ is any of straight chain $C_{12}$, $C_{13}$, $C_{14}$, $C_{15}$, $C_{16}$, $C_{17}$, $C_{18}$ alkyl.

A preferred particle size of 90% of the colloid particles is 10000 nm or less, more preferred of 5000 nm or less.

According to a preferred aspect of the invention particles of larger size than colloid particles and their aqeuous suspensions are comprised by the present invention, such as particles of a size of up to 10 μm or 50 μm and even up to 100 μm, and their suspensions.

The particles of the invention can be separated from the aqueous phase by, for instance, centrifugation or cryoprecipitation. If separated by centrifugation accompanying salt or corresponding ions consisting of the cation of the water soluble alkyl sulfate or alkane sulfonate and of the anion of the anti-cancer drug are eliminated with the aqueous phase. The resulting powder (additionally dried, if necessary) retains the particle size of the colloid to at least 50%, more preferred to at least 80%. To facilitate re-suspension in an aqueous media, the powder can comprise a re-suspension facilitating agent such as glucose, lactose or albumin. Alternatively the particles of the invention can be produced by evaporation, incuding cryoprecipitation, of the aqueous media; in such case they will be admixed with accompanying salt comprising the cation of the water soluble alkyl sulfate or alkane sulfonate and the anion of the anti-cancer drug; if desired they can be admixed with resuspension facilitating agent.

According to another preferred aspect of the invention, colloid particles of the invention can be comprised by micro carrier particles having affinity, such as by including appropriate antibody structures, to a surface antigen of the tumour to be treated.

Preferred pharmacologically active agents D of the amphiphilic sulfonates and sulfates of the invention include but are not limited to doxorubicin, epirubicin, daunorubicin, idarubicin, mitoxantrone, viniblastine, vincristine, vinorelbine, amsacrine, topotecan, irinotecan.

According to a further preferred aspect of the invention, suitable anti-cancer agents for preparing amphiphilic sulfonates and sulfates of the invention other than the aforementioned ones are of similar hydrophilicity as doxorubicin, epirubicin, daunorubicin, idarubicin, mitoxantrone, viniblastine, vincristine, vinorelbine, amsacrine, topotecan, irinotecan.

According to the present invention is also disclosed a method of treating liver cancer in a person, comprising administrating to said person a therapeutically effective amount of the pharmaceutical composition of the inveniton or of a pharmaceutical composition comprising amphiphilic particulate sulfonate or sulfate powder of the invention. A preferred method of administration is by infusion or injection into a vein or artery, in particular into the portal vein or hepatic artery.

Another preferred method of administration is to a solid liver tumour by infusion or injection into the peripheral circulation. A third preferred method of administration is by infusion or injection directly into a solid liver tumour. According to a preferred aspect of the invention administration is by a bolus or by several boli is preferred. One aspect of administration to the liver or liver tumour is by infusion or injection into a vein or artery, in particular into the portal vein or hepatic artery.

According to the present invention is provided a drug delivery system for convenient and non-invasive intravenous administration capable of providing a desired concentration of the drug over extended periods of time, such as for more than one hour or six hours or even a day or more. Such concentration is provided and maintained in the liver or in a solid liver tumour or other tissue. According to a preferred aspect of the invention the invention provides a method of controlling the ratio of distribution of a drug between the liver and other organs and tissues.

In this application, unless otherwise stated, the term "liver disease" (hepatic disease) comprises primary liver cancer (for example hepatocellular carcinoma and/or cholangiocarcinoma, angiosarcoma, hemangiosarcoma of the liver), secondary malignancies (i.e. secondary lesions that have metastasized from primary cancers in the gastrointestinal tract and other organs, such as the kidneys, lungs, breast, or prostate); inflammation of the liver caused by virus (viral hepatitis), liver toxins (e.g. alcoholic hepatitis), autoimmunity (autoimmune hepatitis) or hereditary conditions; liver cirrhosis caused by excessive alcohol consumption.

According to the invention is also disclosed a method of designing a pharmaceutical composition for providing, during a predetermined period, a herapeutic target of a person or animal selected from liver and solid liver tumour with a predetermined concentration of a sulfate or sulfonate of a pharmacologically active agent D comprising from 1 to 4 amino groups represented by formula (1) or (2) or a mixture of these agents:

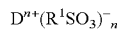  (1)

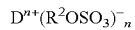  (2)

wherein $R^1$ is straight chain $C_6$-$C_{30}$ alkyl; $R^2$ is straight chain $C_6$-$C_{30}$ alkyl; n is an integer from 1 to 4; wherein the method comprises:
  i) determining the solubility of $D_n^+(R^1SO_3^-)_n$ and/or $D^{n+}(R^2OSO_3^-)n$ for various carbon chain lengths X, Y in an aqueous solvent;
  ii) determining the correlation between the solubility of said sulfate or sulfonate of said pharmacologically active agent and the expected concentration of said pharmaceutically active agent D in the therapeutic target upon administration of said pharmacologically active agent D to the subject or animal;
  iii) defining a target solubility of said sulfate or sulfonate of said pharmacologically active agent in said solvent based on a desired concentration of said pharmaceutically active substance D in said organ or tissue;
  iv) determining the carbon chain length(s) X, Y corresponding to said target solubility;
  v) providing a sulfate or sulfonate of said pharmacologically active agent comprising the so determined the carbon chain length(s) X, Y;
  vi) providing a fluid carrier;
  vii) combining said sulfate or sulfonate of said pharmacologically active agent comprising the so determined the carbon chain length(s) X, Y with the fluid carrier in an amount capable of maintaining said concentration during said period.

According to a preferred aspect of the invention the solubility is determined in an aqueous organic solvent, such as an aqueous alcohol, in particular aqueous ethanol in a concentration of from 5% to 50%, preferably from 10% to 30% (v/v). Other water miscible solvents such as low molecular weight ketones, amides, esters, amides, and sulfoxides may also be used.

According to a preferred aspect of the invention the pharmaceutical composition comprises a mixture of at least two different sulfates or sulfonates of the invention represented by formula (1) or (2) or at least two different sulfates or sulfonates of which one is represented by formula (1) and the other by formula (2).

A preferred pharmacologically active substance D is selected from the group consisting of doxorubicin, epirubicin, daunorubicin, idarubicin, mitoxantrone, viniblastine, vincristine, vinorelbine, amsacrine, topotecan, irinotecan. It is also preferred for the composition to comprise a colloid.

A preferred fluid carrier is water or an aqueous media in which the sulfate or sulfonate of said pharmacologically active agent D is insoluble or substantially insoluble. By "substantially soluble" is understood a solubility of less than 0.1% by weight, in particular of less than 0.05 or 0.02 by weight. The composition may be designed for intraarterial, intraperitoneal, intramuscular, transdermal or intravenous administration. The steps above may be performed in any suitable order.

A preferred form of said sulfate or sulfonate of the pharmacologically active agent D is a powder of a mean particle size (N) of up to 100 μm, preferably up to 50 μm or 10 μm or 5 μm. A preferred form of said pharmaceutical composition is an aqueous suspension, in particular an aqueous colloid.

According to the present invention is also disclosed a method of producing the pharmaceutical composition of the invention, the method comprising: providing a first aqeuous solution of a salt of said anti-cancer drug with an inorganic or organic acid that is not amphiphilic; providing a second aqueous solution comprising an amount of a sodium or potassium salt of an alkyl sulfonate of the formula (Na or K)$^+$(R$^1$SO$_3$)$^-$ or of an alkane sulfate of the formula (Na or K)$^+$(R$_2$OSO$_3$)$^-$ equivalent to the amount of said salt; mixing said first and second solutions. While other than sodium and potassium salts can be used in the method, their use is not preferred. It is preferred for R$^1$ to be straight chain C$_6$-C$_{30}$ alkyl; R$^2$ is straight chain C$_6$-C$_{30}$ alkyl; n is an integer from 1 to 4. It is preferred for R$^1$ and R$^2$ to be straight chain C$_{10}$-C$_{20}$ alkyl, more preferred straight chain C$_{12}$-C$_{18}$ alkyl, most preferred about straight chain Cm alkyl.

According to the present invention is furthermore disclosed the use of the composition of the invention comprising an anti-cancer agent of the group consisting of doxorubicin, epirubicin, daunorubicin, idarubicin, mitoxantrone, viniblastine, vincristine, vinorelbine, amsacrine, topotecan, irinotecan for targeted delivery to the liver of a person or animal.

According to the present invention is also disclosed the use of the amphiphilic particulate sulfonate powder of the invention comprising an anti-cancer agent of the group consisting of doxorubicin, epirubicin, daunorubicin, idarubicin, mitoxantrone, viniblastine, vincristine, vinorelbine, amsacrine, topotecan, irinotecan for the manufacture of a medicament comprising a pharmaceutical composition capable of targeted delivery to the liver of a person or animal.

The invention will now be illustrated in greater detail by a number of non-limiting examples thereof.

Figure 1:
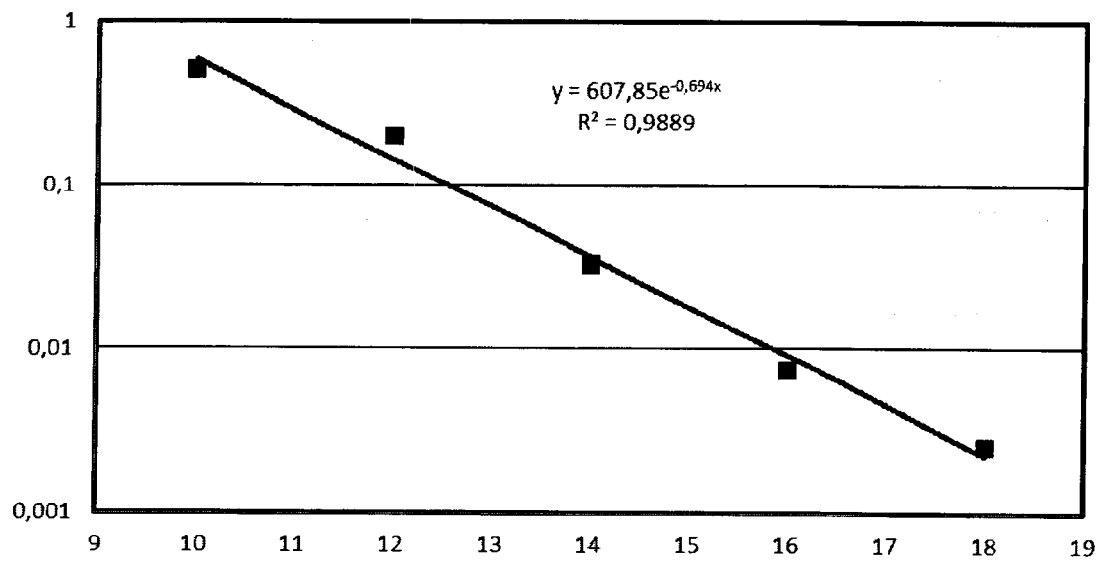
FIG. 1 is a graph illustrating the dependence of the solubility of doxorubicin alkyl sulfate in 30% aqueous ethanol on alkyl chain length.
Figure 2:
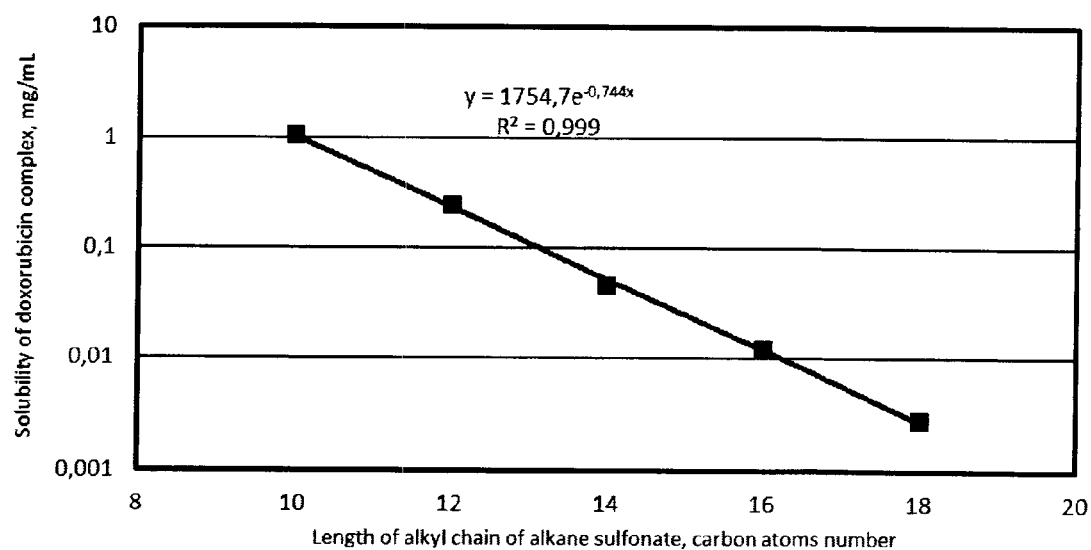
FIG. 2 is a graph illustrating the dependence of the solubility of doxorubicin alkane sulfonate in 30% aqueous ethanol on alkyl chain length.
Figure 3:
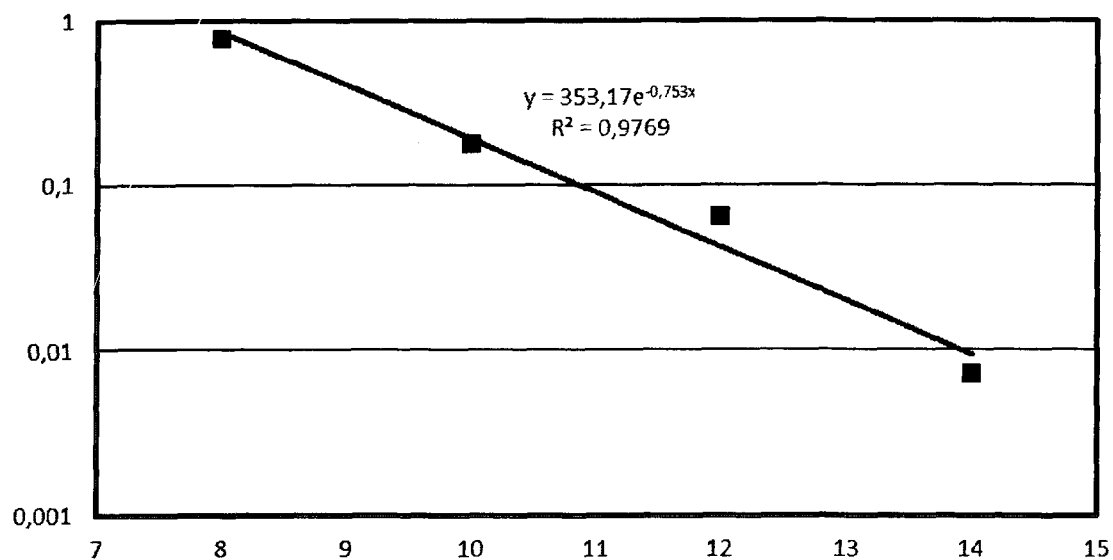
FIG. 3 is a graph illustrating the dependence of the solubility of mitoxantrone alkyl sulfate in 30% aqueous ethanol on alkyl chain length.
Figure 4:
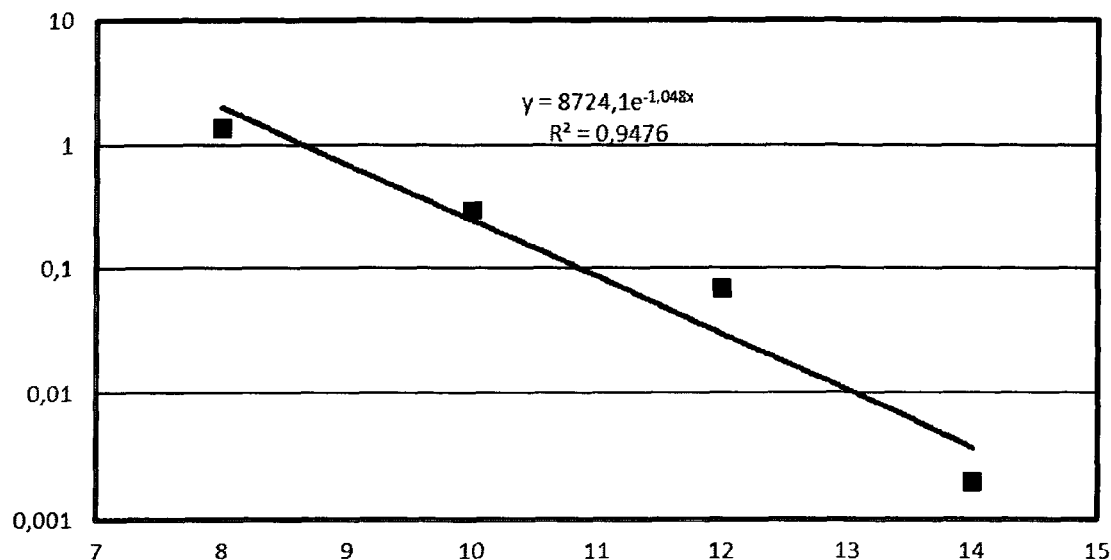
FIG. 4 is a graph illustrating the dependence of the solubility of mitoxanthrone alkane sulfonate in 30% aqueous ethanol on alkyl chain length.
Figure 5:
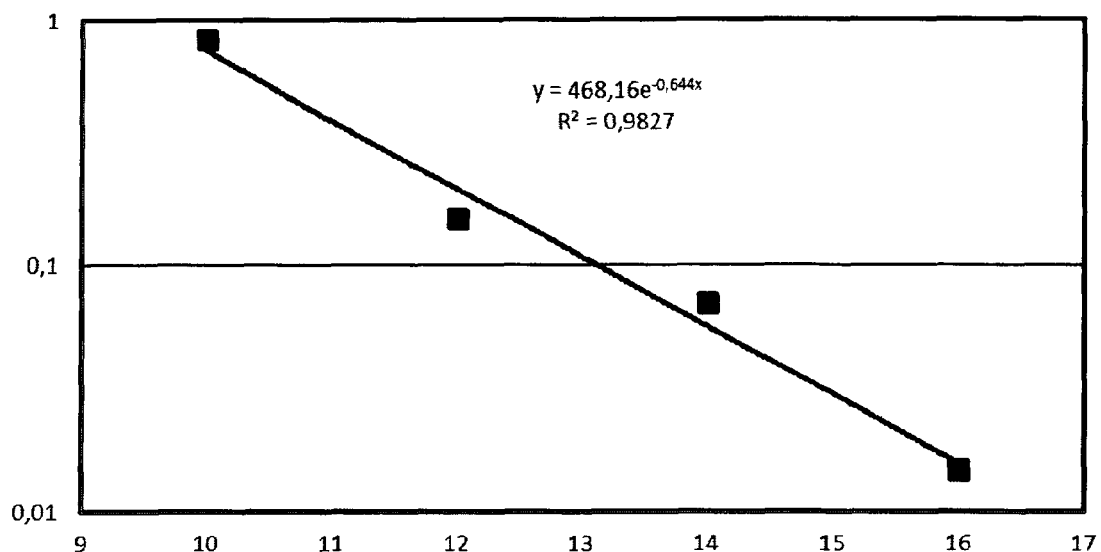
FIG. 5 is a graph illustrating the dependence of the solubility of irinotecan alkane sulfonate in 10% aqueous ethanol on alkyl chain length.
Figure 6:
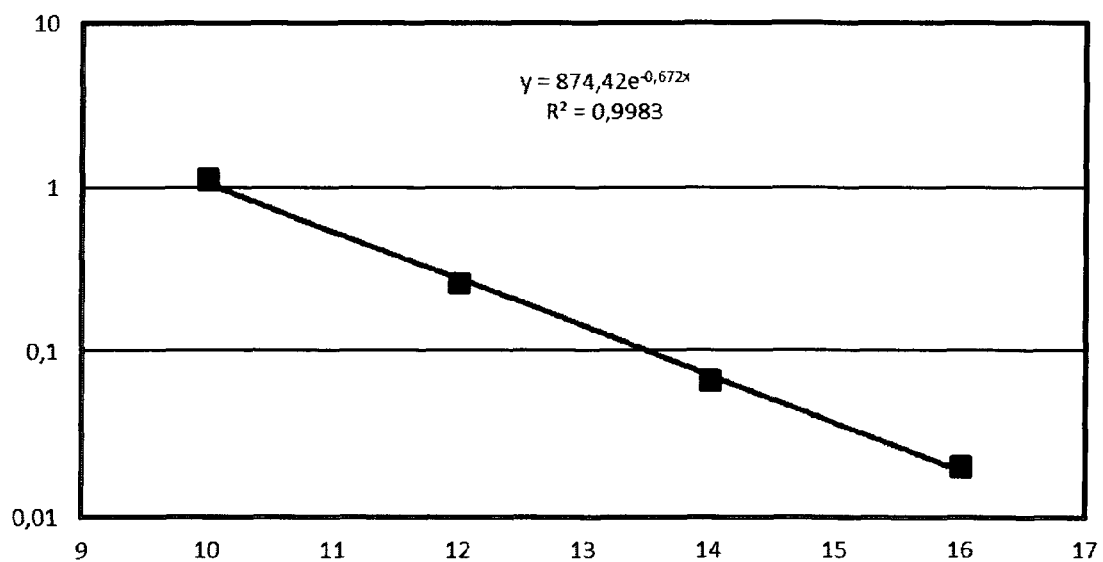
FIG. 6 is a graph illustrating the dependence of the solubility of vinorelbine alkane sulfonate in 20% aqueous ethanol on alkyl chain length.

Exponential (for FIGS. 1-6) and logarithmic (for FIGS. 7 and 8) trendlines and their equations were obtained by means of Microsoft Excel software.

DESCRIPTION OF PREFERRED EMBODIMENTS

General Procedures. Materials and Methods

Solubility in aqueous ethanol was determined by centrifuging an adequate amount of freshly obtained colloid at 3000 rpm for 30-90 min, decanting the supernatant, adding 10 mL water and shaking the mixture, then repeating centrifugation, shaking and washing 3 times. The centrifugate from the final centrifugation was air dried for 72 h at room temperature followed by drying in vacuo for 24 h. A portion of the dried centrifugate (20 mg) was resuspended in 6 mL aqueous ethanol by stirring at room temperature for 24 h. The mixture was centrifuged at 3000 rpm for 10 min and the supernatant filtered through a 0.2 micrometer filter to remove aggregates of undissolved solid product. The solubility of the compound was determined by a UV method.

The composition used for in vivo investigation was freshly prepared or had been obtained by dilution of a concentrate. For in vivo investigation, female Wistar rats 60-75 days old weighing 300 g±30 g were selected. Four animals were used for testing one composition. The doxorubicin compositions were administered via single bolus injections into the tail in an amount of 5 mg/kg doxorubicin. Immediately after sacrificing the rat bodies were deep-frozen in liquid nitrogen.

Determination of the bio-distribution of doxorubicin in liver tissue. Five or six pieces of liver tissue of a total weight of about 1 g were taken from different parts of a liver. The samples were homogenized with a solution of aqueous ethanol containing HCl for 20 s at 7000 rpm and for 10 s at 11000 rpm. The homogenate was vortexed for 30 min and centrifuged at 3000 rpm for 30 min. The supernatant was treated with a solution of monochloroacetic acid and incubated for 1 h. The mixture was centrifuged at 15000 rpm for 15 min. Doxorubicin concentration in the final supernatant was determined by fluorometric analysis.

EXAMPLE 1

Preparation of Colloid Doxorubicin Alkyl Sulfate and Alkane Sulfonate

To a solution of doxorubicin hydrochloride (50 mL, 1 mg/mL) in 5% aqueous dextrose in an Erlenmeyer flask was added at room temperature a solution of a 5-10% molar excess of Na$^+$(R$^1$SO$_3$)$^-$ or Na$^+$(R$^2$OSO$_3$)$^-$ and in the same solvent as for doxorubicin hydrochloride. Instead of 5% aqueous dextrose can be used in this and the other examples Ringer solution or 0.9% saline or phosphate-buffered saline or another aqueous solution of an osmolality from 270 to 300 mOsm/L. The process of colloid formation was monitored visually. After completing of the addition the mixture was vortexed or shaken for an additional time period varying from 30 min to 7 days. The colloid then was either directly used or placed for storage in a refrigerator. Concentration of doxorubicin in the compositions was determined by a UV method at 495 or 233 nm. For sampling, an aliquot of the colloid was diluted with methanol (excess of methanol >20:1).

EXAMPLE 2

Preparation of Colloid Mitoxantrone Alkyl Sulfates and Alkane Sulfonates

To a vigorously stirred solution of mitoxantrone dihydrochloride (40 mL, 0.2 mg/mL) in 5% dextrose in water in an Erlenmeyer flask was added at room temperature a solution containing 0.03 mmol of Na$^+$(R$^1$SO$_3$)$^-$ or Na$^+$(R$^2$OSO$_3$)$^-$ in the same solvent as for mitoxantrone dihydrochloride. The formation of a black colloid was monitored visually. The colloid slowly disintegrated into a black precipitate and a pale supernatant. After completing of the addition the mixture obtained stirred for additional time (from 1 to 7 days). The colloid composition was either used directly or stored in a refrigerator for later use. The concentration of mitoxantrone in the colloid was determined by a UV method at 662, 611 or 242 nm. For sampling an aliquot of the colloid was diluted with methanol to >20:1.

EXAMPLE 3

Preparation of Colloid Irinotecan Alkyl Sulfates and Alkane Sulfonates

To a vigorously solution of irinotecan hydrochloride trihydrate (5 mL, 4 mg/mL) in deionized water was added at room temperature a solution containing $Na^+(R^1SO_3)^-$ or $Na^+(R^2OSO_3)^-$ in deionized water. The formation of a colloid was monitored visually. After completing of the addition the mixture obtained stirred for 2 days and the mixture was centrifuged 10 min at 3000 rpm. On standing the white colloid slowly disintegrated into a white precipitate and a nearly colourless supernatant. The supernatant was replaced by 5% aqeuous dextrose. The precipitate was re-suspended in water by vortexing for 10 min. The composition obtained then was either directly used or stored in a refrigerator for future use. The concentration of irinotecane in the colloid or modified colloid was determined by a UV method at 360, 255 or 220 nm. For sampling an aliquot of the product was diluted with methanol (excess of methanol >20:1).

EXAMPLE 4

Preparation of Colloid Vinorelbine Alkyl Sulfates and Alkane Sulfonates

To a vigorously stirred solution of vinorelbine tartrate (2 mL, 5 mg/mL) in 5% aqueous dextrose in an Erlenmeyer flask was added at room temperature a solution of one equivalent of $Na^+(R^1SO_3)^-$ or $Na^+(R^2OSO_3)^-$ in the same solvent as for vinorelbine tartrate. The formation of a colloid was monitored visually. After completing of the addition the mixture obtained was vortexed or shaken for 7 days. On standing the colloid slowly disintegrated into a precipitate and a clear supernatant. The colloid was either used directly or stored in a refrigerator for future use. The concentration of vinorelbine in the colloid was determined by a UV method at 268 or 212 nm. For sampling an aliquot of the colloid was diluted with methanol (excess of methanol >20:1).

EXAMPLE 5

Solubility of Colloid Doxorubicin Alkyl Sulfates and Alkane Sulfonates in 30% Aqueous Ethanol Solubility was determined in accordance with the general method described under Materials and Methods. The results are summarized in Table 1 and presented in FIGS. 1 and 2.

TABLE 1

Solubility of colloid doxorubicin alkyl sulfates and alkane sufonates in 30% ethanol (v/v)

| Generic formula of anion | Alkyl chain length, n | Solubility, mg/mL |
|---|---|---|
| $C_nH_{2n+1}OSO_3^-$ | 10 | 0.50769 |
| | 12 | 0.20560 |
| | 14 | 0.03281 |
| | 16 | 0.00729 |
| | 18 | 0.00260 |
| $C_nH_{2n+1}SO_3^-$ | 10 | 1.06429 |
| | 12 | 0.23953 |
| | 14 | 0.04596 |
| | 16 | 0.01194 |
| | 18 | 0.00279 |

EXAMPLE 6

Solubility of Colloid Mitoxantrone Alkyl Sulfates and Alkane Sulfonates in 30% Aqueous Ethanol The solubility was determined in accordance with the general method described under Materials and Methods. The results are summarized in Table 4 and presented in FIGS. 3 and 4.

TABLE 2

Solubility of colloid mitoxantrone alkyl sulfates and alkane sufonates in 30% ethanol (v/v)

| Generic formula of anion | Alkyl chain length, n | Solubility, mg/mL |
|---|---|---|
| $C_nH_{2n+1}OSO_3^-$ | 8 | 1.34798 |
| | 10 | 0.29487 |
| | 12 | 0.06813 |
| | 14 | 0.00203 |
| $C_nH_{2n+1}SO_3^-$ | 8 | 0.78058 |
| | 10 | 0.17582 |
| | 12 | 0.06484 |
| | 14 | 0.00720 |

EXAMPLE 7

Solubility of Irinotecan Alkane Sulfonates in 10% Aqueous Ethanol

The solubility was determined in accordance with the general method described under Materials and Methods. The results are summarized in Table 3 and FIG. 5.

TABLE 3

Solubility of colloid irinotecan alkane sufonates in 30% ethanol (v/v)

| Alkyl chain length, n | Solubility, mg/mL |
|---|---|
| 10 | 0.83483 |
| 12 | 0.15453 |
| 14 | 0.07064 |
| 16 | 0.01476 |

EXAMPLE 8

Solubility of Colloid Vinorelbine Alkane Sulfonates in 20% Aqueous Ethanol

The solubility was determined according to the general method described, cf. Materials and Methods. The results are summarized in Table 4 and FIG. 6.

TABLE 4

Solubility of colloid inorelbine alkane sulfonates in 20% aqueous ethanol

| Alkyl chain length, n | Solubility, mg/mL |
|---|---|
| 10 | 1.11868 |
| 12 | 0.25692 |
| 14 | 0.06731 |
| 16 | 0.01977 |

EXAMPLE 9

In Vivo Analysis of Distribution of Doxorubicin in the Liver of Wistar Rats

An aqueous solution of doxorubicin hydrochloride, an aqueous colloid of doxorubicin alkane sulfate and an aqueous colloid of doxorubicin akyl sulfonate were administered via a single bolus injection into the tail Animals were sacrificed after 2 hours after administered via a single bolus injection into the tail; total doxorubicin dose 5 mg/kg. The concentration of doxorubicin in a liver was determined according to the procedure described above.

Figure 7:
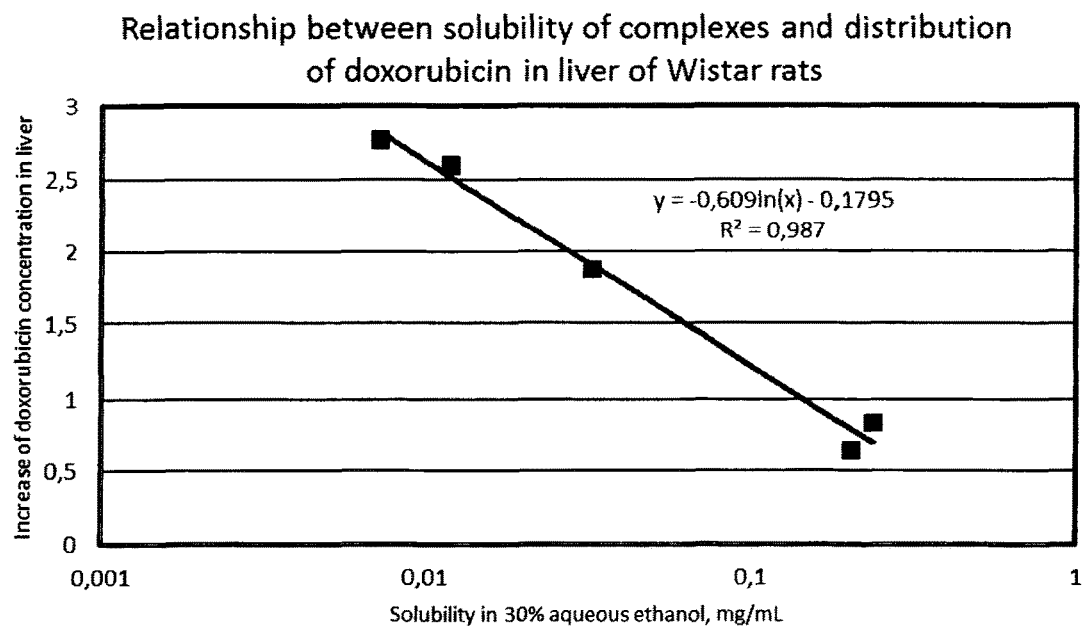
FIG. 7 is a graph illustrating the dependence of doxorubicin concentration in the liver of Wistar rats 2 h post bolus injection on the solubility of doxorubicin alkane sulfate and sulfonate in 30% aqueous ethanol.
Figure 8:
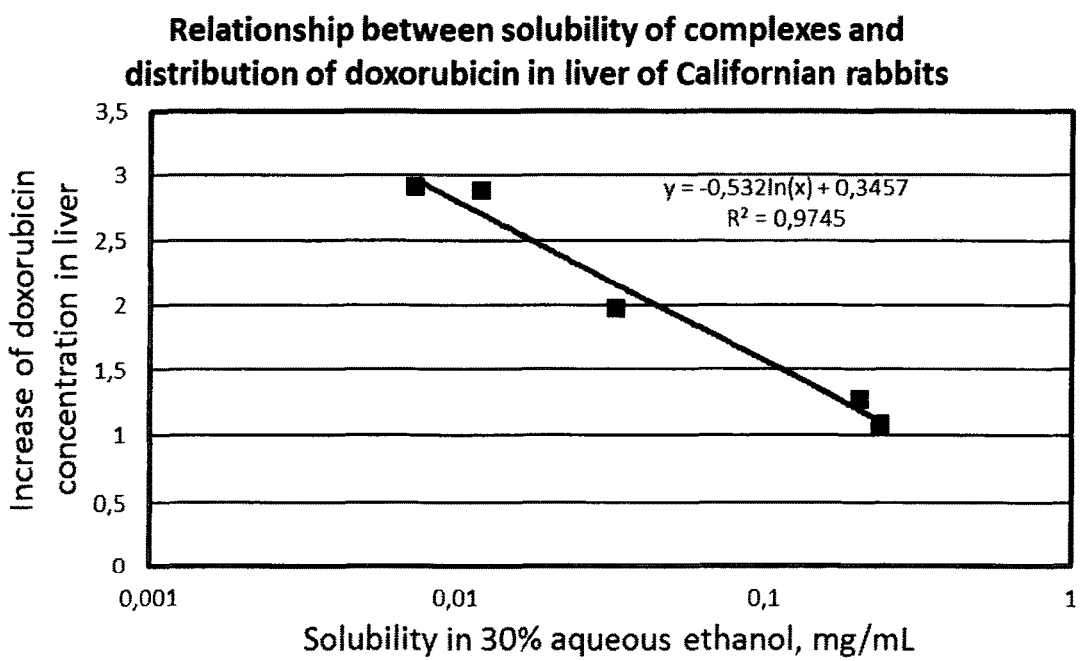
FIG. 8 is a graph illustrating the relationship between the solubility of non-covalent complexes of doxorubicin in 30% aqueous ethanol and the increase of doxorubicin concentration in Californian rabbit liver 0.5 h post intravenous injection.

The results are summarized in Table 5 and FIG. 7.

TABLE 5

In vivo analysis of distribution of doxorubicin in Wistar rat liver

| Anion of doxorubicin salt | Conc. of doxorubicin, µg/kg (SDI) | Solubility in 30% ethanol, mg/mL | Increase of doxorubicin concentration in liver tissue, times |
|---|---|---|---|
| Cl⁻ | 11.47 ± 2.98 | (1) | (1) |
| $(C_{12}H_{25}OSO_3)^-$ | 7.15 ± 2.07 | 0.20560 | 0.64 |
| $(C_{14}H_{29}OSO_3)^-$ | 21.45 ± 4.33 | 0.03281 | 1.87 |
| $(C_{16}H_{33}OSO_3)^-$ | 31.77 ± 2.82 | 0.00729 | 2.77 |
| $(C_{12}H_{25}SO_3)^-$ | 9.52 ± 1.03 | 0.23953 | 0.83 |
| $(C_{16}H_{33}SO_3)^-$ | 29.75 ± 3.51 | 0.01194 | 2.60 |

EXAMPLE 10

In Vivo Analysis of Distribution of Doxorubicin in Californian Rabbit Liver

Colloid non-covalent complexes of doxorubicin and doxorubicin hydrochloride were administered at a slow flow rate of 1 ml/mi to Californian rabbits into the marginal ear vein, the total doxorubicin dose being 5 mg/kg. The animals were sacrificed 0.5 h post administration. The concentration of doxorubicin in a liver was determined in accordance with the procedure described above. For results, see Table 6 and FIG. 8.

TABLE 6

Distribution of doxorubicin in the liver of Californian rabbits

| Anion of doxorubicin salt | Conc. of doxorubicin, µg/kg (SDI) | Solubility in 30% ethanol, mg/mL | Increase of doxorubicin concentration in liver tissue, times |
|---|---|---|---|
| Cl⁻ (Doxorubicin) | 0.392 ± 0.128 | (1) | (1) |
| $C_{12}H_{25}OSO_3$ | 0.496 ± 0.201 | 0.20560 | 1.27 |
| $C_{14}H_{27}OSO_3$ | 0.776 ± 0.301 | 0.03281 | 1.98 |
| $C_{16}H_{33}OSO_3$ | 1.141 ± 0.203 | 0.00729 | 2.91 |

TABLE 6-continued

Distribution of doxorubicin in the liver of Californian rabbits

| Anion of doxorubicin salt | Conc. of doxorubicin, µg/kg (SDI) | Solubility in 30% ethanol, mg/mL | Increase of doxorubicin concentration in liver tissue, times |
|---|---|---|---|
| $C_{12}H_{25}SO_3$ | 0.423 ± 0.078 | 0.23953 | 1.08 |
| $C_{12}H_{25}SO_3$ | 1.128 ± 0.148 | 0.01194 | 2.88 |

EXAMPLE 11

Preparation of a Colloid Comprising Doxorubicin Sulfonates with a Desired Solubility in 30% Aqueous Ethanol This example illustrates the preparation of colloids of the invention with desired solubility in a particular solvent. The following parameters were set: active agent: doxorubicin; anion: alkane sulfonate with even number of carbon atoms; solvent: 30% aqueous ethanol; desired solubility: 0.1 mg/mL.

The calculation was based on the assumption that that the number of carbon atoms in an alkane sulfonate radical of medium chain length is additive. The calculation was furthermore based on the assumption of a continuous function for solubility y in 30% aqueous ethanol.

Following function (f1), which was obtained from Example 5 (cf. FIG. 2) represents relationship between number of carbon atoms x and solubility y.

$$y = f1(x) = 1754.71710 \exp(-0.74429x) \qquad \text{(eq. 1)}$$

Function (f2) allows to perform a reverse calculation, i.e. determine the number of carbon atoms X from a given solubility Y:

$$x = f2(y) = -1/0.7442855697 \ln(y/1754.71709855) \qquad \text{(eq. 2)}$$

For the solubility of y=0.1 mg/mL, the function f2 gives x as equal to 13.20628.

Based on the assumption of an additive effect of the number of carbon atoms in the radicals the ratio of $C_{12}$ and $C_{14}$ sulfonates behaviour (the pair of sulfonates with solubilities closest to the desired one) to provide the suggested C13.20628 radical:

One equivalent of $C_{13.20628}$ is equal to a mixture of 0.397 equivalents of $C_{12}$ and 0.603 equivalents of $C_{14}$.

A mixture of doxorubicin sulfonates with the determined ratio of $C_{12}$ and $C_{14}$ was prepared in accordance the typical method described in Example 1. The solubility was determined in accordance with the general method which is described above, and was found 0.098713 mg/mL.

EXAMPLE 12

Figure 9:
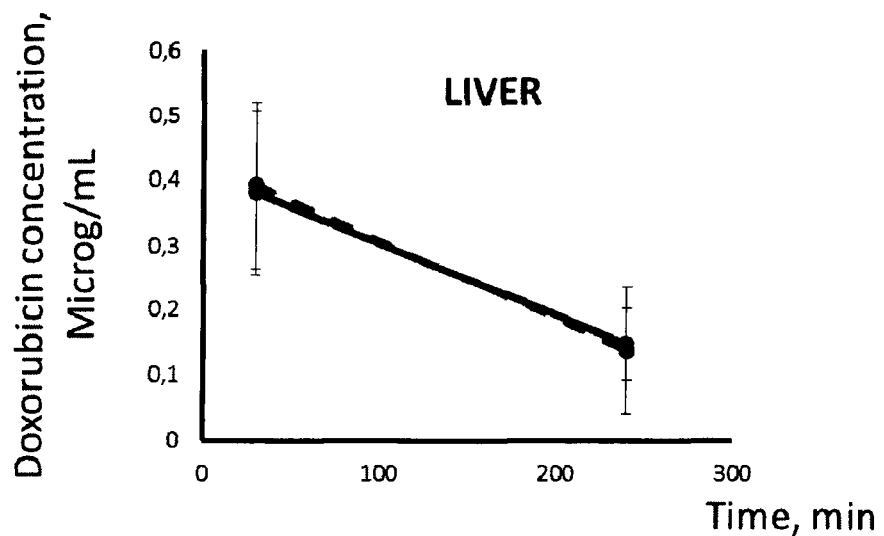
FIG. 9 are graphs illustrating doxorubicin concentration in the liver and the heart upon intravenous injection of 5 mg/kg aqueous doxorubicin hydrochloride and of 1.25 mg/kg of the composition of the invention according to Example 1.
Figure 9:
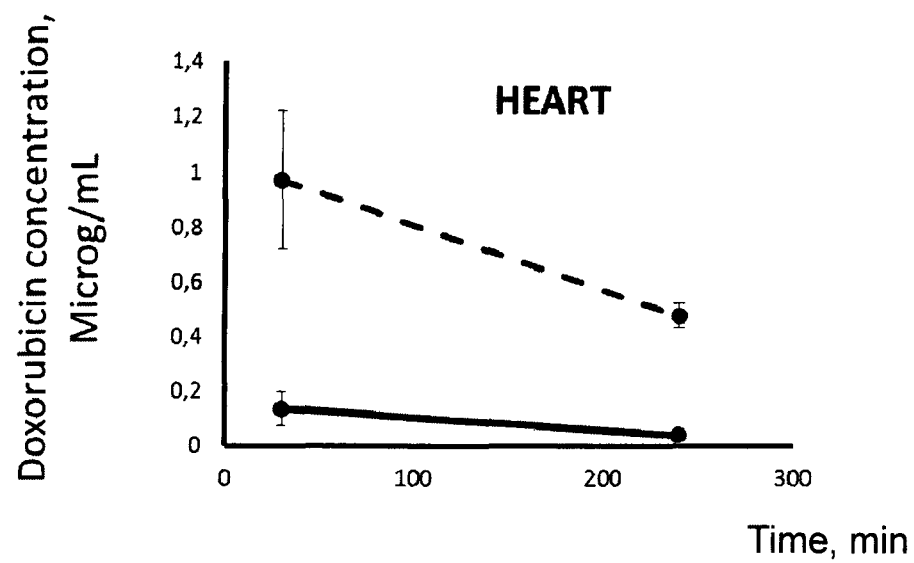

Intravenous Delivery of a Composition of the Invention Targeted to the Liver of Californian Rabbits The doxorubicin composition of the invention according to Example 1 (R=$C_{16}$ sulfonate) was administered to Californian rabbits by injection into the ear vein at a concentration of 1.25 mg doxorubicin/kg body weight. For comparison aqueous doxorubicin hydrochloride was administered in the same manner at a concentration of 5.0 mg doxorubicin/kg body weight. As shown by FIG. 9 the composition of the invention is about four times more efficient in regard of delivery of doxorubicin to the liver than prior art aqueous doxorubicin hydrochloride, whereas there is no difference in regard of delivery to the heart.

The invention claimed is:

1. Pharmaceutical composition in the form of an aqueous colloid comprising solid particles consisting of amphiphilic sulfonate particles of a hydrophilic anti-cancer agent or amphiphilic sulfate particles of a hydrophilic anti-cancer agent, the particles having a solubility in water or aqueous body fluid of less than 0.1% by weight, wherein 90% or more of the particles have a size of 10,000 nm or less.

2. The composition of claim 1, wherein the solid particles consist of amphiphilic sulfonate particles of a hydrophilic anti-cancer agent.

3. The composition of claim 1, wherein the solid particles consist of amphiphilic sulfate particles of a hydrophilic anti-cancer agent.

4. The composition of claim 2, further comprising buffer and/or pharmaceutically acceptable excipient.

5. The composition of claim 2, wherein the amphiphilic sulfonate consists of a pharmacologically active anti-cancer agent D comprising from 1 to 4 amino groups of which one or more is protonated, and of a corresponding number of sulfonate anion.

6. The composition of claim 3, wherein the amphiphilic sulfate consists of a pharmacologically active anti-cancer agent D comprising from 1 to 4 amino groups of which one or more is protonated, and of a corresponding number of sulfate anion.

7. The composition of claim 2, wherein the amphiphilic sulfonate is represented by formula (1): $D^{n+}(R^1SO_3)^-_n$ (1); wherein $R^1$ is straight chain $C_6$-$C_{30}$ alkyl; n is an integer from 1 to 4.

8. The composition of claim 3, wherein the amphiphilic sulfate is represented by formula (2): $D^{n+}(R^2OSO_3)^{31}_n$ (2); wherein $R^2$ is straight chain $C_6$-$C_{30}$ alkyl; n is an integer from 1 to 4.

9. The composition of claim 7, wherein $R^1$ is straight chain $C_{10}$-$C_{20}$ alkyl.

10. The composition of claim 5, wherein D is selected from the group consisting of doxorubicin, epirubicin, daunorubicin, idarubicin, mitoxantrone, vinblastine, vincristine, vinorelbine, amsacrine, topotecan, irinotecan.

11. A method of producing the pharmaceutical composition of claim 2 comprising: providing a first aqueous solution of a salt of said hydrophilic anti-cancer agent with an inorganic or organic acid that is not amphiphilic; providing a second aqueous solution comprising an amount of a sodium or potassium salt of an alkyl sulfonate of the formula (Na or K)$^+$(R$^1$SO$_3$)$^{31}$ equivalent to the amount of said salt of said hydrophilic anti-cancer agent; and mixing said first and second solutions to form solid particles consisting of amphiphilic sulfonate particles of the hydrophilic anti-cancer agent.

12. A method of producing the pharmaceutical composition of claim 3 comprising: providing a first aqueous solution of a salt of said hydrophilic anti-cancer agent with an inorganic or organic acid that is not amphiphilic; providing a second aqueous solution comprising an amount of a sodium or potassium salt of an alkyl sulfate of the formula (Na or K)$^+$(R$^2$OSO$_3$)$^{31}$ equivalent to the amount of said salt of said hydrophilic anti-cancer agent; and mixing said first and second solutions to form solid particles consisting of amphiphilic sulfate particles of the hydrophilic anti-cancer agent.

13. The method of claim 11, wherein $R^1$ is straight chain $C_6$-$C_{30}$ alkyl and n is an integer from 1 to 4.

14. The method of claim 11, wherein $R^2$ is straight chain $C_6$-$C_{30}$ alkyl; n is an integer from 1 to 4.

15. The method of claim 13, wherein $R^1$ is straight chain $C_{10}$-$C_{20}$ alkyl.

16. The method of claim 14, wherein $R^2$ is straight chain $C_{10}$-$C_{20}$ alkyl.

17. A method of treating cancer in a person, comprising administering to said person a therapeutically effective amount of the pharmaceutical composition of claim 1.

18. The method of claim 17, wherein administration is by infusion or injection into a vein or artery.

19. The method of claim 17, wherein administration is to a solid liver tumour by infusion or injection into the peripheral circulation.

20. The method of claim 17, wherein administration is by infusion or injection directly into a solid liver tumour.

21. The method of claim 17, wherein administration is by a bolus or by several boli.

22. The composition of claim 1, wherein the hydrophilic anti-cancer agent is selected from the group consisting of doxorubicin, epirubicin, daunorubicin, idarubicin, mitoxantrone, vinblastine, vincristine, vinorelbine, amsacrine, topotecan, and irinotecan.

23. The composition of claim 1, wherein the particles have a solubility in water or aqueous body fluid of less than 0.05% by weight.

24. The composition of claim 1, wherein the particles have a solubility in water or aqueous body fluid of less than 0.02% by weight.

25. The composition of claim 1, wherein 90% or more of the particles have a size of 5000 nm or less.

26. The composition of claim 7, wherein $R^1$ is straight chain $C_{12}$-$C_{18}$ alkyl.

27. The composition of claim 7, wherein $R^1$ is $C_{16}$.

28. The composition of claim 2, further comprising osmolality controlling agent and/or viscosity controlling agent.

29. The method of claim 17, wherein administration is by infusion or injection into the portal vein or hepatic artery.

* * * * *

UNITED STATES PATENT AND TRADEMARK OFFICE
CERTIFICATE OF CORRECTION

PATENT NO. : 10,034,838 B2
APPLICATION NO. : 15/509875
DATED : July 31, 2018
INVENTOR(S) : Igor Lakot It is certified that error appears in the above-identified patent and that said Letters Patent is hereby corrected as shown below:

On the Title Page

Item "(30) Foreign Application Priority Data", change "1400427" to --1400427-9--.

Signed and Sealed this
Thirtieth Day of October, 2018

Andrei Iancu
*Director of the United States Patent and Trademark Office*